United States Patent [19]
Campeta

[11] Patent Number: 6,077,871
[45] Date of Patent: *Jun. 20, 2000

[54] DROLOXIFENE PHARMACEUTICAL COMPOSITIONS

[75] Inventor: Anthony M. Campeta, Ledyard, Conn.

[73] Assignee: Pfizer Inc., New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 09/109,447

[22] Filed: Jul. 2, 1998

Related U.S. Application Data

[60] Provisional application No. 60/066,600, Nov. 26, 1997.

[51] Int. Cl.$^7$ .................................................. A61K 31/135
[52] U.S. Cl. ................................................................ 514/648
[58] Field of Search .............................................. 514/648

[56] References Cited

U.S. PATENT DOCUMENTS

| | | | |
|---|---|---|---|
| 5,047,431 | 9/1991 | Schickaneder et al. | 514/648 |
| 5,254,594 | 10/1993 | Niikura et al. | 514/648 |
| 5,550,164 | 8/1996 | Fontana | 514/648 |

FOREIGN PATENT DOCUMENTS

| | | |
|---|---|---|
| 0658348 | 6/1995 | European Pat. Off. . |
| WO9002141 | 3/1990 | WIPO . |
| WO9311757 | 6/1993 | WIPO . |
| WO9416733 | 8/1994 | WIPO . |

OTHER PUBLICATIONS

F. Hirayama, et al., J. Pharamaceutical Sciences, vol. 81, No. 8, Aug. 1992, pp. 817–822, "Prominent Inculsion Effect of Dimethyl–β–cyclodextrin on Photoisometrization of the Thromboxane Synthetase Inhibitor (E–4–(1–Imidazoylmenthyl)cinnamic Acid".

P. Bortolus, et al., J. Phys. Chem, 1987, 91, pp. 5046–5050, CIS ⇌ Trans Photoisomerization of Azobenzene–Cyclodextrin Inclusion Complexes.

T. Loftsson, et al., Pharmaceutical Sciences, Oct. 1996, vol. 85, No. 10, pp. 1017–1025, "Pharmaceutical Applications of Cyclodextrins. 1. Drug Solubilization and Stabilization".

E. Pop, et al., PHarmaceutical Research, vol. 8, No. 8, 1991, pp. 1044–1049, "Solubilization and Stabilization of Benzylpenicillin Chemical Delivery System by 2–Hydroxpropyl–β–cyclodextrin".

B. Gorecka, et al, International Journal of Pharmaceutics 125(1995) pp. 55–61, "Effect of SBE4–β –CD, a sulfobutyl ether β–cyclodextrin, on the stability and solubility of $O^6$–benzylguanine (NSC–637037) in aqueous solutions".

M. Brewster, et al., Pharmaceutical Research, vol. 8, No. 6, 1991, pp. 792–795, "Use of 2–Hydroxypropyl–β–cyclodextrin as a Solubilizing and Stabilizing Excipient for Protein Drugs".

F. Hirayama, et al., Duchene, D., Ed.; Editions de Sante: Paris 1987; Chapter 4, pp. 131–172, "Cyclodextrins and their Industrial Uses".

J. Szejtli, Pharmaceutical Technology, Aug. 1991, pp. 24–38, "Cyclodextrins in Drug Formulations: Part II".

G. Duveneck, et al., J. Phys. Chem, 1989, 93, pp. 7166–7170, "Picosecond Laser Studies on Photochemical Reactions in Restricted Environments: The Photoisomerization of trans–Stilbene Complexed to Cyclodextrins".

H. Helm, et al., European Journal of Pharmaceutical Sciences 3 (1995) pp. 195–201, "Complexation of dihydroergotamine mesylate with cyclodextrin derivatives: Solubility and stability in aqueous solution".

B.W. Muller, et al., In: Proc. 4th Int. Symp. Cyclodextrins, 369–382 (1988) "Cyclodextrin Derivatives for Solubilisation, Stabilisation, and Absorption of Drugs".

*Primary Examiner*—James H. Reamer
*Attorney, Agent, or Firm*—Peter C. Richardson; Gregg C. Benson; A. Dean Olson

[57] ABSTRACT

Compositions of matter comprising droloxifene or a pharmaceutically acceptable salt thereof and a cyclodextrin. Preferred cyclodextrins are SBECD and HPBCD. The composition can comprise a dry mixture, a dry inclusion complex or an aqueous solution. The citrate salt of droloxifene is preferred.

12 Claims, No Drawings

DROLOXIFENE PHARMACEUTICAL COMPOSITIONS

This is a continuation of provisional application U.S. Ser. No. 60/066,600 filed Nov. 26, 1997, the benefit of which is hereby claimed under 37 C.F.R. §1.78(a)(3).

BACKGROUND OF THE INVENTION

This invention relates to droloxifene pharmaceutical compositions.

Droloxifene is disclosed in U.S. Pat. No. 5,047,431 (the disclosure of which is hereby incorporated by reference) as an anti-tumor agent, particularly for treatment of cancer of the breast. Droloxifene is also useful for the relief of bone diseases caused by the deficiency of estrogen or the like, which are often observed in women after menopause or those with the ovaries removed (U.S. Pat. No. 5,254,594 (the disclosure of which is hereby incorporated by reference)).

Formulation of pharmaceutical dosage forms is frequently hampered by poor aqueous solubility and/or stability of the drug of interest, which in turn can severely limit its therapeutic application. Conversely, increasing drug solubility and stability through appropriate formulation can lead to increased therapeutic efficiency of the drug. Various methods have been used to increase the solubility and stability of drugs such as the use of organic solvents, emulsions, liposomes and micelles, chemical modifications, and complexation of drugs with appropriate complexing agents such as cyclodextrins.

Cyclodextrins, sometimes referred to as Schardinger's dextrins, were first isolated by Villiers in 1891 as a digest of *Bacillus amylobacter* on potato starch. The foundations of cyclodextrin chemistry were laid down by Schardinger in the period 1903–1911. Until 1970, however, only small amounts of cyclodextrins could be produced in the laboratory and the high production cost prevented the usage of cyclodextrins in industry. In recent years, dramatic improvements in cyclodextrin production and purification have been achieved and cydodextrins have become much less expensive, thereby making the industrial application of cyclodextrins possible.

Cyclodextrins are capable of forming inclusion complexes with a wide variety of hydrophobic molecules by taking up a whole molecule (a "guest molecule"), or some part of it, into the void cavity. The stability of the resulting complex depends on how well the guest molecule fits into the cyclodextrin cavity.

The following published patents describe the use of cyclodextrins to stabilize pharmaceutical compounds:
WO 9311757;
WO 9002141;
WO 9416733; and
EP 658348.

The following articles describe the use of cyclodextrins to stabilize compounds which undergo an isomerization reaction:
Hirayama, F et al. *J Pharm Sci*, 81, 817, (1992);
Duveneck, G et al. *J Phys Chem*, 93, 7166, (1989); and
Bortolus, P et al. *J Phys Chem*, 91, 5046 (1987).

The following are general articles on the solubilization and stabilization of pharmaceutical compounds using cyclodextrins:
Loftsson, T. et al. *J. Pharm Sci*, 85, 1017 (1996);
Helm, H et al. *Eur Pharm Sci*, 3, 195 (1995);
Muller, B W et al. *In: Proc, 4th Int. Symp. Cyclodextrins*, 369–82 (1988);
Pop, E et al. *Pharm Res.*, 8, 1044 (1991);
Gorecka, B et al. *Int J Pharm*, 125, 55 (1995); and
Brewster, M et al. *Pharm. Res*, 8, 792 (1991).

The following article reviews the methods of preparation of compound-cyclodextrin complexes:
Hirayama, F. et al. In *Cyclodextrins and their Industrial Uses*; Duchene, D., Ed.; Editions de Sante: Paris 1987; Chapter 4, pp131–172.

Although cyclodextrins have been used to increase the solubility, dissolution rate and/or stability of a great many compounds, it is also known there are many compounds for which cyclodextrin complexation either is not possible or yields no advantages (J. Szejtli, Cyclodextrins in Drug Formulations: Part II, *Pharmaceutical Technology*, 24–38, August, 1991).

SUMMARY OF THE INVENTION

This invention is directed to compositions of matter comprising a cyclodextrin and a compound of Formula I (droloxifene)

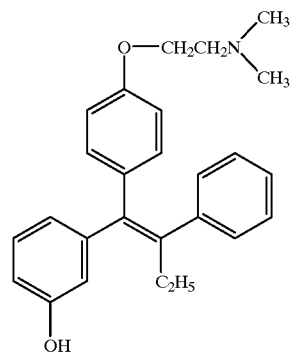

Formula I or a pharmaceutically acceptable salt thereof.

Preferably the pharmaceutically acceptable salt is the citrate salt.

Preferably, the composition is a dry mixture.

Preferably, the composition is a dry inclusion complex.

Preferably, the composition is an aqueous solution of an inclusion complex.

Preferably, the cyclodextrin in any of the above compositions is a β-cyclodextrin and it is especially preferred that the cyclodextrin is B-cyclodextrin (underivatized) hydroxypropyl-β-cyclodextrin (HPBCD) or sulfobutylether-beta-cyclodextrin (SBECD).

The compositions can be administered orally, for example as a tablet or capsule or solution or parenterally, for example, as an injectable or by inhalation to a mammal (e.g., human male or female) in need thereof.

The phrase "composition(s) of matter" as used herein including the appendant claims encompasses, inter alia, compositions of droloxifene and a cyclodextrin which are dry physical mixtures, which are dry inclusion complexes, or which are aqueous solutions of dissolved inclusion complexes. For example, a composition can comprise a dry mixture of droloxifene physically mixed with a dry cyclodextrin for reconstitution for use as a liquid formulation intended for oral administration. A composition, in a preferred embodiment, can also comprise an aqueous or other solution which has been lyophilized or otherwise dried (e.g., in a vacuum oven or other suitable device), such that the composition comprises a dry, pre-formed inclusion complex of cyclodextrin-complexed droloxifene which can later be re-constituted before oral or parenteral dosing, or which can be dosed orally in a capsule or tablet. A composition can also comprise the aqueous solution itself, i.e., a droloxifene plus cyclodextrin plus water. Inclusion complexes are thus within the scope of the term "composition of matter" whether they are pre-formed, formed in situ, or formed in vivo.

The phrase "mgA" indicates the weight (in mg) of droloxifene calculated as the free base, (for droloxifene, molecular weight =387.52).

DETAILED DESCRIPTION OF THE INVENTION

The preparation of droloxifene (1-[4'-(2-dimethylaminoethoxy)phenyl]-1-(3'-hydroxyphenyl)-2-phenylbut-1-ene) and pharmaceutically acceptable salts thereof is described in U.S. Pat. No. 5,047,431.

The pharmaceutically acceptable acid addition salts of droloxifene are non-toxic salts, such as salts with organic acids (e.g., formic, acetic, trifluoroacetic, citric, maleic, tartaric, methanesulfonic, benzenesulfonic or toluenesulfonic acids, with citrate being preferred), inorganic acids (e.g. hydrochloric, hydrobromic, sulfuric or phosphoric acids), and amino acids (e.g., aspartic or glutamic acids).

The pharmaceutically acceptable acid addition salts of droloxifene can be prepared as known in the art by conventional methodology by treating a solution or suspension of droloxifene free base with about one chemical equivalent or a slight excess of a pharmaceutically acceptable acid. The salt can be isolated by conventional methods, such as by filtration when the salt spontaneously precipitates, e.g., as a crystalline material or, particularly if the salt is amorphous, it can be isolated by concentration and/or addition of a non-solvent.

The use of droloxifene is disclosed for the treatment of a variety of disease/conditions including breast cancer, and bone diseases such as osteoporosis.

Any cyclodextrin may be used in this invention. The following descriptions of cyclodextrins are meant as exemplary rather than limiting. Cyclodextrins are cyclic oligosaccharides with hydroxyl groups on the outer surface and a void cavity in the center. Their outer surface is hydrophilic, and therefore they are usually soluble in water, but the cavity has a lipophilic character. The most common cyclodextrins are $\alpha$-cyclodextrin, $\beta$-cyclodextrin and $\gamma$-cyclodextrin, consisting of 6, 7 and 8 $\alpha$-1,4-linked glucose units, respectively. The number of these units determines the size of the cavity.

Useful cyclodextrins include $\alpha$, B, and $\gamma$ cyclodextrins, methylated cyclodextrins, hydroxypropyl-B-cyclodextrin (HPBCD), hydroxyethyl-B-cyclodextrin (HEBCD), branched cyclodextrins in which one or two glucose or maltose moieties are enzymatically attached to the cyclodextrin ring, ethyl- and ethyl-carboxymethyl cyclodextrins, dihydroxypropyl cyclodextrins, and sulfoalkyl ether cyclodextrins. The degree of substitution is not considered to be critical, and the cyclodextrins just mentioned can have essentially any degree of substitution (per entire cyclodextrin molecule) as known in the art. The hydroxyl groups of beta-cyclodextrin are often chemically modified to increase the solubility of the cyclodextrin as well as the complex formed with the host molecule. Mixtures of cyclodextrins, as well as single species, are feasible for making dosage forms according to the invention.

Two highly soluble (500 mg/mL) commercial cyclodextrins, B-cyclodextrin sulfobutyl ether (SBECD) and hydroxypropyl B-cyclodextrin (HPBCD) are preferred for use in this invention. HPBCD and SBECD are preferred for both oral and parenteral administration. HPBCD is well known in the art; see for example Publication R 81 216 entitled "Encapsin HPB" from Janssen Biotech N.V. SBECD is also known and has been disclosed in U.S. Pat. Nos. 5,376,645 and 5,134,127, both to Stella et al. and both are herein incorporated by reference.

Typically, cyclodextrin derivatives are formed by alkylation (e.g., methyl-and-ethyl-$\beta$-cyclodextrin) or hydroxyalkylation of the hydroxyethyl-derivatives of $\alpha$-, $\beta$-, and $\gamma$-cyclodextrin) or by substituting the primary hydroxyl groups with saccharides (e.g., glucosyl- and maltosyl-$\beta$-cyclodextrin). Hydroxypropyl-$\beta$-cyclodextrin and its preparation by propylene oxide addition to $\beta$-cyclodextrin, and hydroxyethyl-$\beta$-cyclodextrin and its preparation by ethylene oxide addition to $\beta$-cyclodextrin, are described in U.S. Pat. No. 3,459,731, the disclosure of which is hereby incorporated by reference.

An amount of droloxifene is used such that the composition provides the desired therapeutic effect. Droloxifene may be administered once to four times a day with a unit dosage of 0.25 mg to 100 mg in human patients for both oral or parenteral administration, but the above dosage may be properly varied depending on the age, body weight and medical condition of the patient and the type of administration. One dose per day is preferred.

Solid formulations may include tablets or capsules, or oral powders intended for reconstitution with water prior to dosing. A mixture of a cyclodextrin and droloxifene as a solid inclusion complex, typically, may be used as fill for a capsule or compressed into a tablet for oral administration. Upon exposure to an aqueous environment of use such as the luminal fluid of the gastrointestinal tract or the salivary fluid of the buccal cavity, this inclusion complex aids in increasing bioavailability relative to the uncomplexed drug. These formulations typically contain other components known to those skilled in the art such as fillers, disintegrants, binders, lubricants, dispersing agents, thickening agents as well other excipients such as dyes and flavorings. Examples of such components are provided in the Examples.

For liquid formulations, cyclodextrins serve a dual purpose of enhancing the stability as well as solubility of droloxifene. Liquid formulations for example, include oral solutions, oral suspensions, parenteral solutions and parenteral lyophiles. The solubility enhancement effect from cyclodextrins facilitates the attainment of a solution dosage form having the desired dosage. Oral liquid formulations may contain other excipients known to those skilled in the art such as thickening agents, dispersing agents, dyes and flavorings. Liquid formulations may also contain buffers, antioxidants, preservatives and tonicity adjusters. Typical buffers include phosphates, acetates, citrates and glycine. Examples of antioxidants include ascorbic acid, sodium bisulfite, sodium metabisulfite, monothioglycerol, thiourea, butylated hydroxytoluene, butylated hydroxy anisole, and ethylenediaminetetraacetic acid salts. Preservatives useful in liquid formulations include benzoic acid and its salts, sorbic acid and its salts, alkyl esters of parahydroxybenzoic acid, phenol, chlorobutanol, benzyl alcohol, thimerosal, benzalkonium chloride and cetylpyridinium chloride. The buffers mentioned previously as well as dextrose, glycerin and sodium chloride can be used for tonicity adjustment if necessary.

A solid inclusion complex of droloxifene can be formed by conventional methods. That is, an excess amount of droloxifene is added to an aqueous cyclodextrin solution until an equilibrium solubility is attained. The water is ultimately removed by evaporative techniques and the remaining solid dried to yield the drug-cyclodextrin complex. Alternatively, the complex may be precipitated from aqueous solution by addition of a solvent in which the complex is minimally soluble or insoluble. The molar ratio of the droloxifene inclusion complex can vary depending on initial solution concentrations of each component. In general, the amount of cyclodextrin in a formulation is such that the molar ratio of cyclodextrin to droloxifene is between 0.1:1 to 20:1, preferably 0.5:1 to 10:1, more preferably 1:1 to 4:1.

As a solid formulation, the cyclodextrin:droloxifene range is generally from 120:1 to 1:2, preferably 40:1 to 1:1, more preferably 20:1 to 1:1 w/w.

If the formulation is an aqueous solution, it can contain cyclodextrin in a wide range of concentrations. The preferred cyclodextrin concentration for a liquid formulation will be dependent upon the droloxifene dose and pH of solution. However, generally, the preferred range of cyclodextrins in such aqueous solutions is 0.2–50% weight to volume. Cyclodextrin can be present in an amount over that needed to complex the droloxifene completely.

An inclusion complex for a liquid formulation of droloxifene can be formed by conventional methods. That is, a desired inclusion complex of droloxifene can be formed in situ by adding droloxifene, in an amount up to the amount corresponding to its equilibrium solubility (or less depending on the desired strength of the product solution), directly to a pre-made solution of cyclodextrin dissolved in water (or other suitable pharmaceutically acceptable aqueous medium). A combination comprising sterile water (or other pharmaceutically acceptable aqueous medium such as a buffer), cyclodextrin, and droloxifene dissolved therein is sufficient to form a product solution which can be parenterally administered directly to human patients. This product solution, after sterile filtration, can be used as is for administration to patients immediately, no adjustment to isotonicity being required, or stored at 5° C. for periods up to two years and longer. For a liquid formulation the concentration of droloxifene is generally 0.2 mgA/mL to 150 mgA/mL, preferably 1 mgA/mL to 125 mgA/mL, more preferably 5 mgA/mL to 100 mgA/mL.

Alternatively, the inclusion complex of droloxifene in cyclodextrin can first be isolated by drying, usually by lyophilization. The isolated dry inclusion complex can be stored at room temperature for periods up to two years and longer, and reconstituted into a product solution as needed. When a product solution is required, it can be made by dissolving the isolated inclusion complex in water (or other aqueous medium) in an amount sufficient to generate a solution of the required strength for oral or parenteral administration to patients. If parenteral administration is the chosen route of administration, intramuscular injection is preferred.

For further examples of excipients and exemplary methods of preparing pharmaceutical compositions, see *Remington's Pharmaceutical Sciences*, Mack Publishing Company, Easter, Pa., 15th Edition (1975).

Cyclodextrin/droloxifene mixtures were examined and found to demonstrate enhanced solubility and stability as follows:

The solubility of droloxifene citrate was determined in an aqueous phosphate buffer at pH 3, without and with various levels of cyclodextrins. Solubility testing of droloxifene citrate in solutions of the cydodextrins, SBECD and HPBCD, was conducted using an equilibrium solubility method. The following protocol was employed for the solubility determination. The HPBCD was purchased commercially from Janssen Biotech N.V. (Belgium). The SBECD employed had a degree of substitution with sulfobutyl groups of 6.5, average per molecule of β-cyclodextrin, and was made by a process analogous to that described in Example 3 of U.S. Pat. No. 5,376,645.

Separate 0.02 M aqueous buffer solutions of phosphoric acid ($H_3PO_4$) and 0.02 M dibasic sodium phosphate ($Na_2HPO_4$) were prepared by dissolving 2.25 gm and 2.84 gm, respectively, into separate one liter portions of deionized water and stirring with a magnetic stir bar until dissolved. To obtain a pH 3 buffer, the two previous buffers were combined, at an approximate ratio of 2:1 ($H_3PO_4$ buffer:$Na_2HPO_4$ buffer). The final volume of the resulting pH 3 buffer was not critical.

To 25 mL volumetric flasks, weights of either HPBCD or SBECD were added to produce final concentrations of each cyclodextrin shown in Table 1. For example, to prepare a 2% w/v solution of HPBCD in pH 3 phosphate buffer, 0.5 gm of HPBCD was accurately added to a 25 mL volumetric flask. Approximately 90% of the total volume was made with the buffer, and the flask swirled until dissolution of the cyclodextrin was complete, usually within 15 minutes. Sufficient buffer was then added to complete the solution, and the flask was inverted several times to achieve a homogeneous solution.

To 5 mL glass vials with screw caps, 3 mL of the desired cyclodextrin solution was added. An excess of solid droloxifene citrate was added to each vial. The vial contents were mixed for three days at ambient temperature to allow sufficient time for equilibrium to be established. After the three days, the vials contained undissolved solids indicating a saturated solution under the conditions employed. The contents were filtered into a clean screw cap vial through a Millex-HV 0.45 µm filter (Millipore, Bedford, Mass.) and the drug concentration determined by an HPLC method.

As an example of an HPLC assay used to determine droloxifene solubility, the amount of dissolved droloxifene was determined using C18 Ultrasphere (Registered trademark of Beckman) (Fullerton, Calif.) column with an isocratic mobile phase consisting of 45% water, 31% methanol, 24% acetonitrile and 0.15% trifluoroacetic acid. The mixture was adjusted to pH 3 with ammonium hydroxide. The mobile phase was delivered at a flow rate of 1.5 mL/min at 30° C. Detection was by UV absorption at a wavelength of 230 nm. Quantification was effected facilely by comparison of HPLC peak area with the peak area taken from a standard plot of concentration versus peak area for standards of known concentration. As is conventional, the droloxifene standard concentrations were selected to fall within a linear range of concentration versus absorbance for the UV detector employed. The saturated equilibrium solution obtained after filtering the test vial solutions was diluted in serial fashion to reach the linear range of the standard plot. Dilution was effected by adding isocratic mobile phase.

The results detailed in Table 1 (below) demonstrate an enhancement of droloxifene citrate solubility with cyclodextrin.

TABLE 1

| Cyclodextrin | Concentration (% w/v) | Droloxifene Solubility (mg/mL) | Solubility Increase |
|---|---|---|---|
| NONE | 0 | 0.11 | — |
| HPBCD | 0.75 | 0.67 | 6× |
| HPBCD | 2.0 | 3.00 | 27× |
| HPBCD | 4.0 | 6.79 | 62× |
| HPBCD | 7.0 | 10.6 | 96× |
| HPBCD | 10.0 | 12.6 | 115× |
| HPBCD | 14.0 | 17.0 | 154× |
| SBECD | 3.3 | 4.31 | 39× |
| SBECD | 6.5 | 8.12 | 74× |
| SBECD | 11.6 | 13.4 | 122× |
| SBECD | 16.2 | 17.4 | 158× |
| SBECD | 23.1 | 26.3 | 239× |

The stability of droloxifene citrate was determined at pH 3 with various concentrations of SBECD and HPBCD. For this protocol, the 0.02 M sodium phosphate buffer of pH 3 and the cyclodextrin solutions were prepared as for the droloxifene solubility determination described previously. 10 mL of each cyclodextrin solution was added to an 18 mL clear glass vial with screw cap which contained a previously weighed amount of droloxifene citrate. The vials were swirled until dissolution of droloxifene citrate was complete. The concentration of droloxifene citrate ranged from 0.05–0.1 mgA/mL. Concentrations of HPBCD included 0.2, 2, 4, 7 and 10% w/v. Concentrations of SBECD included 0.33 and 3.3% w/v. The vials were stored in an 840 foot-candle fluorescent light box at 30° C. The solutions were removed briefly from time to time to allow drug concentration determination using the HPLC method described as for the solubility determination.

The results in Table 2 (below) show a stability enhancement of droloxifene with the inclusion of cyclodextrins. The concentration of cyclodextrin that results in the greatest stabilizing effect depends on the efficiency of the formation of the droloxifene-cyclodextrin inclusion complex, that is, the stability constant, as well as the initial concentration of droloxifene present. This test, which is carried out in the presence of an intense light source, demonstrates a 1.3–4× improvement in stability, which is very useful for assuring cyclodextrin stability after reconstitution in solution, for example, in a hospital environment. This stability improvement is further useful for preconstituted aqueous solutions which must have a long practical shelf-life, e.g., 2 years, even if packaged in a partially light-protected package. Droloxifene is significantly more stable out of light, however an improvement in stability is also observed in light-protected solutions with beta-cyclodextrins present. While not wishing to be held to any theory, it is believed that incorporation of droloxifene in the cyclodextrin cavity minimizes a cis-trans isomerization reaction, thus reducing the formation of the isomeric decay product and resulting in an overall stability improvement.

TABLE 2

| Solution | Decay Rate Constant (hr$^{-1}$) | Time Required for 1% Decay | Stability Enhancement |
|---|---|---|---|
| No cyclodextrin | 0.0123 | 0.8 hours | — |
| 2% HPBCD | 0.0030 | 3.3 hours | 4× |
| 3.3% SBECD | 0.0070 | 1.4 hours | 1.8× |
| 0.2% HPBCD | 0.0094 | 1.1 hours | 1.3× |
| 0.33% SBECD | 0.0090 | 1.1 hours | 1.3× |

The following examples are possible formulations:

EXAMPLE 1

Formulation for 40 mg droloxifene tablet

| COMPONENT | MG/TABLET | MG/TABLET |
|---|---|---|
| Droloxifene citrate* | 59.79** | 59.79** |
| HPBCD* | 140.0 | — |
| SBECD* | — | 220.0 |
| Dicalcium Phosphate | 130.21 | 100.21 |
| Corn Starch | 30.0 | 30.0 |
| Magnesium stearate/Sodium lauryl sulfate (90:10) | 5.0 | 5.0 |
| TOTAL | 365.0 | 415.0 |

*Present as a droloxifene-cyclodextrin inclusion complex
**Based on 66.9% of droloxifene in droloxifene citrate salt

EXAMPLE 2

Formulation for 40 mg droloxifene oral solution (40 mg droloxifene/teaspoon)

| COMPONENT | WEIGHT (MG) /TEASPOON |
|---|---|
| Droloxifene citrate | 59.79* |
| SBECD or HPBCD | 400.00 |
| Sucrose | 5000.00 |
| Monobasic sodium phosphate | 15.00 |
| Hydroxypropyl cellulose (Klucel-EF) | 12.00 |
| Xanthan Gum (Keltrol) | 12.00 |
| Spray Dried Cherry #11929 | 34.35 |
| S.D. Art Banana #15223 | 56.25 |
| Art Creme de Vanilla #11489 | 76.25 |
| Sodium benzoate | 18.75 |
| FD&C Red #40 | 0.35 |
| Purified Water | to make 5 mL |

*Based on 66.9% of droloxifene in droloxifene citrate salt

EXAMPLE 3

Formulation for 60 mg droloxifene parenteral solution (60 mg droloxifene / 2 ml)

| COMPONENT | WEIGHT (MG) / 2 ML |
|---|---|
| Droloxifene citrate | 89.69* |
| SBECD or HPBCD | 600.00 |
| Monobasic sodium phosphate | 20.00 |
| Methyl paraben | 1.50 |
| Monothioglycerol | 4.00 |
| Sterile Water for Injection | to make 2 ML |

*Based on 66.9% of droxoxifene in droloxifene citrate salt

What is claimed is:

1. A composition of matter comprising an inclusion complex of a compound of the Formula I Formula I

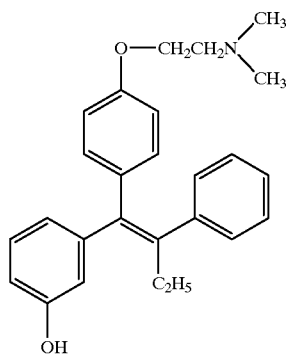

or a pharmaceutically acceptable salt thereof and a cyclodextrin.

2. A composition as recited in claim 1 wherein the Formula I compound is the citrate salt.

3. A composition as recited in claim 2 wherein said composition is a dry inclusion complex of said compound with said cyclodextrin.

4. A composition as recited in claim 2 wherein said composition is an aqueous solution of an inclusion complex of said compound with said cyclodextrin.

5. A composition as recited in claim 1 wherein said cyclodextrin is a β-cyclodextrin.

6. A composition as recited in claim 5 wherein said β-cyclodextrin is β-cyclodextrin, HPBCD or SBECD.

7. A composition of matter comprising an inclusion complex of a pharmaceutically acceptable salt of a compound of Formula I

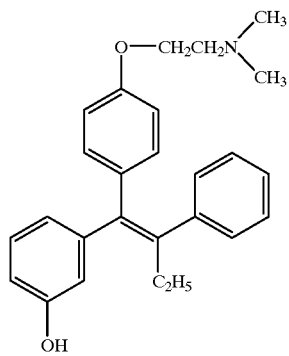

in a cyclodextrin.

8. An inclusion complex as recited in claim 7 wherein the salt of the compound of Formula I is the citrate salt.

9. A composition as recited in claim 8 wherein said cyclodextrin is a β-cyclodextrin.

10. A composition as recited in claim 9 wherein said β-cyclodextrin is HPBCD or SBECD.

11. A composition as recited in claim 6 wherein said cyclodextrin is HPBCD or SBECD.

12. A composition as recited in claim 10 wherein said cyclodextrin is HPBCD or SBECD.

* * * * *